(12) United States Patent
Bettati et al.

(10) Patent No.: US 7,452,899 B2
(45) Date of Patent: Nov. 18, 2008

(54) GAMMA-SECRETASE INHIBITORS

(75) Inventors: Michela Bettati, Sawbridgeworth (GB); Amanda Louise Boase, London (GB); Ian Churcher, Royston (GB); Tamara Ladduwahetty, London (GB); Kevin John Merchant, Ware (GB); Abdul Quddus, Harlow (GB)

(73) Assignee: Merck Sharp & Dohme Limited, Hoddesdon, Hertfordshire (GB)

( * ) Notice: Subject to any disclaimer, the term of this patent is extended or adjusted under 35 U.S.C. 154(b) by 332 days.

(21) Appl. No.: 10/566,486

(22) PCT Filed: Jul. 29, 2004

(86) PCT No.: PCT/GB2004/003277

§ 371 (c)(1),
(2), (4) Date: Jan. 30, 2006

(87) PCT Pub. No.: WO2005/014553

PCT Pub. Date: Feb. 17, 2005

(65) Prior Publication Data

US 2006/0189666 A1    Aug. 24, 2006

(30) Foreign Application Priority Data

Aug. 5, 2003    (GB)    ................ 0318447.0

(51) Int. Cl.
| A01N 43/42 | (2006.01) |
| A01N 47/00 | (2006.01) |
| A61K 31/44 | (2006.01) |
| A61K 31/21 | (2006.01) |
| A61K 31/26 | (2006.01) |
| A61K 43/64 | (2006.01) |
| C07D 215/00 | (2006.01) |
| C07D 217/00 | (2006.01) |

(52) U.S. Cl. ............... 514/278; 514/514; 514/342; 514/359; 514/406; 514/396; 514/364; 514/374; 546/15; 546/268.7; 548/377.1; 548/376.1; 548/373.1; 548/215

(58) Field of Classification Search ............... 514/278, 514/514, 342, 359, 406, 396, 364, 374; 546/15, 546/268.7; 548/377.1, 376.1, 373.1, 235, 548/215
See application file for complete search history.

(56) References Cited

FOREIGN PATENT DOCUMENTS

| WO | 01/70677 | * | 9/2001 |
| WO | WO 01/70677 | | 9/2001 |
| WO | WO 02/36555 | | 5/2002 |
| WO | WO 03/093251 | | 11/2003 |

OTHER PUBLICATIONS

Dewachter et al., Lancet Neurology (2002), 1(7), 409-416.*

* cited by examiner

*Primary Examiner*—D. Margaret Seaman
*Assistant Examiner*—Niloofar Rahmani
(74) *Attorney, Agent, or Firm*—William Krovatin; Raynard Yuro

(57) ABSTRACT

Compounds of Formula (I): inhibit the processing of APP by gamma-secretase, and hence are useful for treatment or prevention of Alzheimer's disease.

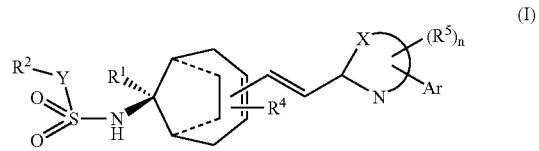

7 Claims, No Drawings

GAMMA-SECRETASE INHIBITORS

CROSS REFERENCE TO RELATED APPLICATIONS

This application is a U.S. National Phase application under 35 U.S.C. § 371 of PCT application Ser. No. PCT/GB2004/003277, filed Jul. 29, 2004, which claims priority under 35 U.S.C. § 119 from GB application Ser. No. 0318447.0, filed Aug. 5, 2003.

The present invention relates to a novel class of compounds, their salts, pharmaceutical compositions comprising them, processes for making them and their use in therapy of the human body. In particular, the invention relates to novel sulphonamide and sulphamide derivatives which inhibit the processing of APP by γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ). The role of secretases, including the putative γ-secretase, in the processing of amyloid precursor protein (APP) to form Aβ is well documented in the literature and is reviewed, for example, in WO 01/70677.

There are relatively few reports in the literature of compounds with inhibitory activity towards γ-secretase, as measured in cell-based assays. These are reviewed in WO 01/70677. Many of the relevant compounds are peptides or peptide derivatives.

WO 01/70677 and WO 02/36555 disclose, respectively, sulphonamido- and sulphamido-substituted bridged bicycloalkyl derivatives which are believed to be useful in the treatment of Alzheimer's disease, but do not disclose or suggest compounds in accordance with the present invention.

The present invention provides a novel class of bridged bicycloalkyl sulphonamide and sulphamide derivatives which show a particularly strong inhibition of the processing of APP by the putative γ-secretase, and thus are useful in the treatment or prevention of AD.

According to the invention there is provided a compound of formula 1:

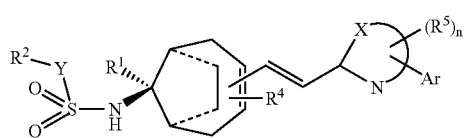

wherein n is 0 or 1;

X completes a 5- or 6-membered heteroaromatic ring bearing the group Ar as a substituent, and also the group $R^5$ as a substituent when n is 1;

$R^5$ represents a hydrocarbon group of 1-5 carbon atoms which is optionally substituted with up to 3 halogen atoms;

Ar represents phenyl or 6-membered heteroaryl, either of which bears 0-3 substituents independently selected from halogen, $CF_3$, $CHF_2$, $CH_2F$, $NO_2$, CN, $OCF_3$, $C_{1-6}$alkyl and $C_{1-6}$alkoxy;

Y represents a bond or $NR^3$;

$R^1$ represents H, or when Y represents $NR^3$, $R^1$ and $R^3$ may together represent —$CH_2$—;

$R^2$ represents a hydrocarbon group of 1-10 carbon atoms which is optionally substituted with up to 3 halogen atoms, or heteroaryl of 5 or 6 ring atoms optionally bearing up to 3 substituents independently selected from halogen, $CF_3$, $CHF_2$, $CH_2F$, $NO_2$, CN, $OCF_3$, $C_{1-6}$alkyl and $C_{1-6}$alkoxy; or when Y represents $NR^3$, $R^2$ and $R^3$ together may complete a heterocyclic ring of up to 6 members which optionally bears up to 3 substituents independently selected from halogen, $CF_3$, $CHF_2$, $CH_2F$, $NO_2$, CN, $OCF_3$, $C_{1-6}$alkyl and $C_{1-6}$alkoxy;

$R^3$ represents H or $C_{1-4}$alkyl, or together with $R^1$ represents —$CH_2$—, or together with $R^2$ completes a heterocyclic ring as defined above; and $R^4$ represents halogen or $C_{1-4}$alkyl;

or a pharmaceutically acceptable salt thereof.

In formula I, the group $R^4$ and the vinylic moiety comprising X and Ar are attached to opposite ends of the ring double bond, and it will be apparent to those skilled in the art that this results in the compounds of formula I existing in two enantiomeric forms, represented by formulae Ia and Ib:

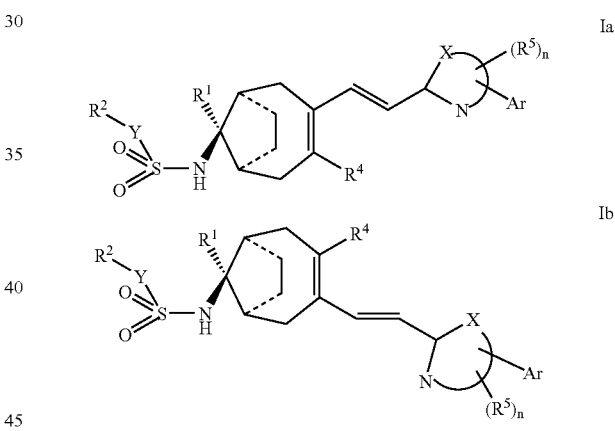

where X, Y, Ar and $R^1$—$R^4$ have the same meanings as before.

It is to be emphasised that the invention, for each compound in accordance with formula I, encompasses both enantiomeric forms, either as homochiral compounds or as mixtures of enantiomers in any proportion.

Where a variable occurs more than once in formula I or in a substituent thereof, the individual occurrences of that variable are independent of each other, unless otherwise specified.

As used herein, the expression "hydrocarbon group" refers to groups consisting solely of carbon and hydrogen atoms. Such groups may comprise linear, branched or cyclic structures, singly or in any combination consistent with the indicated maximum number of carbon atoms, and may be saturated or unsaturated, including aromatic when the indicated maximum number of carbon atoms so permits.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner. Most suitably, the number of carbon atoms in such groups is not more than 6.

The expression "$C_{3-6}$cycloalkyl" as used herein refers to nonaromatic monocyclic hydrocarbon ring systems comprising from 3 to 6 ring atoms. Examples include cyclopropyl, cyclobutyl, cyclopentyl, cyclohexyl and cyclohexenyl.

The expression "cycloalkylalkyl" as used herein includes groups such as cyclopropylmethyl, cyclobutylmethyl, cyclopentylmethyl and cyclohexylmethyl.

The term "halogen" as used herein includes fluorine, chlorine, bromine and iodine, of which fluorine and chlorine are preferred.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In the compounds of formula I, X completes a 5- or 6-membered heteroaromatic ring bearing the group Ar as a substituent, and optionally the group $R^5$ as a substituent. Five-membered rings completed by X preferably comprise at least one heteroatom, selected from O, N and S, in addition to the nitrogen atom shown in formula 1. Suitable five-membered rings include pyrazole, oxazole, isoxazole, thiazole, isothiazole, imidazole, triazole, oxadiazole and thiadiazole, of which pyrazole, oxazole, thiazole, imidazole and 1,2,4-triazole are preferred. Suitable 6-membered rings include pyridine, pyrimidine and pyrazine, of which pyridine is preferred.

The optional substituent $R^5$ is a hydrocarbon group of 1-5 carbon atoms which is optionally substituted with up to 3 halogen atoms, and thus may comprise cyclic or acyclic hydrocarbon residues or combinations thereof, saturated or unsaturated, up to a maximum of 5 carbon atoms in total. The hydrocarbon group represented by $R^5$ is preferably unsubstituted or is substituted with up to 3 fluorine atoms Examples include methyl, ethyl, n-propyl, isopropyl, n-butyl, sec-butyl, t-butyl, fluoromethyl, difluoromethyl, trifluoromethyl, 2,2,2-trifluoroethyl, cyclopropyl, cyclopropylmethyl and allyl. Preferred examples include methyl, ethyl and 2,2,2-trifluoroethyl. Most preferably, $R^5$ represents methyl. $R^5$ may be attached to a ring carbon atom or to a ring nitrogen atom when valency constraints so permit, including to the nitrogen atom shown in formula I although this is not preferred.

Ar represents phenyl or 6-membered heteroaryl, either of which bears 0-3 substituents independently selected from halogen, $CF_3$, $CHF_2$, $CH_2F$, $NO_2$, CN, $OCF_3$, $C_{1-6}$alkyl and $C_{1-6}$alkoxy. Examples of suitable 6-membered heteroaryl groups represented by Ar include pyridyl, pyrazinyl, pyrimidinyl, pyridazinyl and triazinyl, of which pyridyl is a preferred example. Preferably, the phenyl or heteroaryl ring bears 0 to 2 substituents. Preferred substituents include halogen (especially chlorine and fluorine), CN, $C_{1-6}$alkyl (especially methyl), $C_{1-6}$alkoxy (especially methoxy), $OCF_3$ and $CF_3$. If two or more substituents are present, preferably not more than one of them is other than halogen or alkyl. Examples of groups represented by Ar include phenyl, monohalophenyl, dihalophenyl, trihalophenyl, cyanophenyl, methylphenyl, methoxyphenyl, trifluoromethylphenyl, trifluoromethoxyphenyl, pyridyl, monohalopyridyl and trifluoromethylpyridyl, wherein "halo" refers to fluoro or chloro. Suitable specific values for Ar include 2-fluorophenyl, 2-chlorophenyl, 3-fluorophenyl, 4-fluorophenyl, 4-chlorophenyl, 2,4-difluorophenyl, 2,4-dichlorophenyl, 3,4-difluorophenyl, 3,4-dichlorophenyl, 3-chloro-4-fluorophenyl, 3,4,5-trifluorophenyl, 4-cyanophenyl, 4-methylphenyl, 4-methoxyphenyl, 2-(trifluoromethyl)phenyl, 4-(trifluoromethyl)phenyl, 4-(trifluoromethoxy)phenyl, pyridin-2-yl, pyridin-3-yl, pyridin-4-yl, pyrazin-2-yl, 5-methylpyridin-2-yl, 5-fluoropyridin-2-yl, 5-chloropyridin-2-yl, 5-(trifluoromethyl)pyridin-2-yl and 6-(trifluoromethyl)pyridin-3-yl. Preferred examples include 2-fluorophenyl, 2-chlorophenyl, 3-fluorophenyl, 4-fluorophenyl, 4-chlorophenyl, 2,4-difluorophenyl, 2,4-dichlorophenyl, 3,4-difluorophenyl, 3,4-dichlorophenyl, 3-chloro-4-fluorophenyl, 4-(trifluoromethyl)phenyl, pyridin-2-yl, pyridin-3-yl and pyridin-4-yl.

In a particularly preferred embodiment, Ar represents 4-fluorophenyl.

Ar may be attached to a ring carbon or ring nitrogen, preferably in a 1,3-relationship to the double bond which links the ring completed by X to the remainder of the molecule.

Preferred examples of heteroaryl groups completed by X include 5-aryl-1-methylpyrazol-3-yl, 5-aryloxazol-2-yl, 4-arylpyridin-2-yl, 1-arylimidazol-4-yl, and 1-aryl-[1,2,4]triazol-3-yl, where "aryl" refers to the group Ar having the definition and preferred identities indicated above. A particularly preferred example is 5-(4-fluorophenyl)-1-methylpyrazol-3-yl.

$R^4$ represents halogen (especially Cl, Br or I) or $C_{1-4}$alkyl, such as methyl, ethyl, isopropyl, n-propyl or n-butyl. Preferably $R^4$ represents Cl or methyl. In a particular embodiment $R^4$ represents Cl.

Y represents a bond or $NR^3$. When Y represents $NR^3$, $R^3$ optionally combines with $R^1$ to form a —$CH_2$— group. Otherwise, $R^1$ is H. When $R^1$ and $R^3$ combine in this manner, the result is a spiro-linked cyclic sulfamide of formula II:

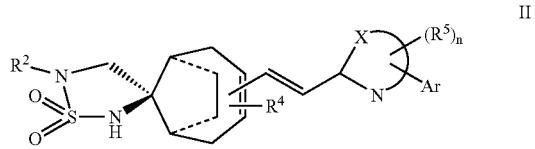

II where n, X, $R^2$, $R^4$, $R^5$ and Ar have the same definitions and preferred identities as before.

$R^2$ represents an optionally-substituted hydrocarbon group as defined previously. Suitable hydrocarbon groups represented by $R^2$ include alkyl, cycloalkyl, cycloalkylalkyl, alkenyl, phenyl and benzyl groups optionally bearing up to 3 halogen substituents, the preferred halogen substituent being fluorine or chlorine, especially fluorine. Said alkyl, cycloalkyl, cycloalkylalkyl and alkenyl groups typically comprise up to 6 carbon atoms. Examples of hydrocarbon and fluorinated hydrocarbon groups represented by $R^2$ include 4-fluorophenyl, benzyl, n-propyl, 2,2-dimethylpropyl, n-butyl, isopropyl, t-butyl, 2,2,2-trifluoroethyl, 3,3,3-trifluoropropyl, allyl, 2-methylpropen-3-yl, cyclopropyl, cyclobutyl, cyclopentyl and cyclopropylmethyl.

Heteroaryl groups represented by $R^2$ are either 5-membered or 6-membered and are optionally substituted as defined previously. Preferred 5-membered heteroaryl groups include those containing a sulphur atom, such as thienyl, thiathiazolyl and isothiazolyl. Preferred 6-membered heteroaryl groups include pyridyl, in particular 3-pyridyl. Preferred substituents include halogen (especially chlorine or fluorine), $CF_3$ and allyl (such as methyl). If two or more substituents are present, preferably not more than one of them is other than halogen or alkyl. Preferred heteroaryl groups are unsubstituted or monosubstituted with halogen.

When $R^2$ represents an optionally substituted phenyl or heteroaryl group, Y is preferably a bond.

When Y represents $NR^3$, $R^2$ may combine with $R^3$ to complete a heterocyclic ring of up to 6 members which is optionally substituted as defined previously. Said ring preferably comprises at most one heteroatom selected from O, N and S in addition to the nitrogen to which $R^2$ and $R^3$ are mutually attached. Suitable rings include azetidinyl, pyrrolidinyl, piperidinyl, piperazinyl, morpholinyl and thiomorpholinyl. Preferred substituents include $CF_3$, halogen (especially chlorine or fluorine) and alkyl such as methyl. If two or more substituents are present, preferably not more than one of them is other than halogen or alkyl.

$R^3$ may alternatively represent H or $C_{1-4}$alkyl, such as methyl. Preferably, $R^3$ represents H or completes a ring with $R^2$ or with $R^1$.

In one subset of the compounds of formula I, Y is a bond and $R^2$ is hydrocarbon of up to 6 carbon atoms, optionally bearing up to 3 fluorine or chlorine substituents, or 5- or 6-membered heteroaryl which is optionally substituted as described previously. Within this subset, suitable identities for $R^2$ include methyl, n-butyl, 4-fluorophenyl, 2-thienyl, 5-chloro-2-thienyl, 5-isothiazolyl and 6-chloro-3-pyridyl. Preferred identities for $R^2$ include 6-chloro-3-pyridyl.

In a second subset of the compounds of formula I, Y is NH and $R^2$ represents alkyl, alkenyl, cycloalkyl or cycloalkylalkyl of up to 6 carbon atoms which is optionally substituted with up to 3 fluorine atoms. Within this subset, preferred identities for $R^2$ include n-propyl, n-butyl, 2-methylpropen-3-yl, cyclobutyl and 2,2,2-trifluoroethyl.

In a third subset of the compounds of formula I, Y represents $NR^3$ and $R^2$ and $R^3$ complete a heterocyclic ring as described previously, in particular a pyrrolidine ring.

A fourth subset of the compounds of formula I is defined by formula II above in which $R^2$ represents alkyl, alkenyl, cycloalkyl or cycloalkylalkyl of up to 6 carbon atoms which is optionally substituted with up to 3 fluorine atoms. Within this subset, suitable identities for $R^2$ include, n-propyl, 2,2-dimethylpropyl, n-butyl, isopropyl, t-butyl, 2,2,2-trifluoroethyl, 3,3,3-trifluoropropyl, allyl, cyclobutyl and cyclopropylmethyl, in particular allyl, cyclopropylmethyl, n-propyl, n-butyl, cyclobutyl and 2,2,2-trifluoroethyl.

Individual compounds in accordance with the invention are illustrated in the Examples section later herein.

The compounds of the present invention have an activity as inhibitors of γ secretase.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

The present invention also provides a compound of the invention or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of the present invention or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to the present invention or a pharmaceutically acceptable salt thereof.

For treating or preventing Alzheimer's disease, a suitable dosage level is about 0.01 to 250 mg/kg per day, preferably about 0.01 to 100 mg/kg per day, more preferably about 0.05 to 50 mg/kg of body weight per day, and for the most preferred compounds, about 0.1 to 10 mg/kg of body weight per day. The compounds may be administered on a regimen of 1 to 4 times per day. In some cases, however, a dosage outside these limits may be used.

For the sake of clarity, synthetic routes to compounds of the invention will be shown as providing compounds of formula Ia, but as will be readily apparent to those skilled in the art, the described procedures actually provide a racemic mixture of compounds of formulae Ia and Ib, unless Steps are taken to isolate one of the intermediates in homochiral form for use in the remainder of the synthetic scheme.

Compounds of formula II may be prepared by methods analogous to those disclosed in WO 02/36555. However, a preferred route involves reaction of an amine $R^2NH_2$ with an aziridine of formula (1a):

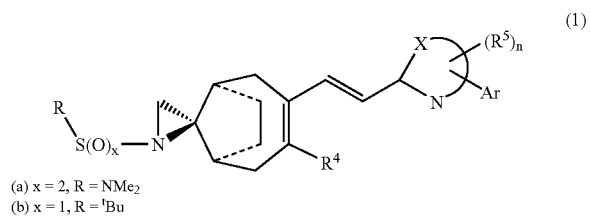

(a) x = 2, R = $NMe_2$
(b) x = 1, R = $^tBu$ where n, X, $R^2$, $R^4$, $R^5$ and Ar have the same meanings as before. The reaction may be carried out in DMSO at 100° C. in a sealed tube.

Alternatively, the compounds of formula II may be obtained by sequential treatment of an aziridine of formula (1b) with an amine $R^2NH_2$ and then $NH_2SO_2NH_2$. Reaction of (1b) with the amine may be carried out in refluxing dichloromethane in the presence of zinc iodide, and reaction of the resulting diamine may with sulfamide may be carried out in refluxing pyridine.

Aziridines (1a) may be prepared by condensation of ketones (2) with $Me_2NSO_2NH_2$ and reaction of the resulting sulphimine with trimethylsulfoxonium iodide:

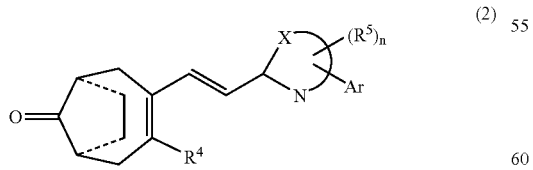

where n, X, $R^4$, $R^5$ and Ar have the same meanings as before. The condensation may be carried out in refluxing THF in the presence of $Ti(OEt)_4$, while reaction to form the aziridine (1) takes place in DMSO at ambient temperature in the presence of sodium hydride.

Aziridines (1b) may be prepared in the same manner, substituting $tBuSONH_2$ for $Me_2NSO_2NH_2$.

Compounds of formula I in which $R^1$ is H may be prepared by reaction of $R^2$—Y—$SO_2Cl$ with an amine of formula (3):

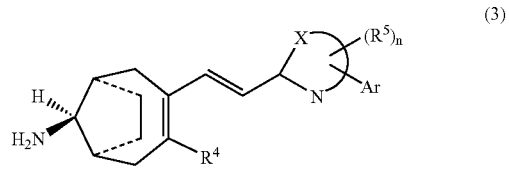

where $R^2$, Y, n, X, $R^4$, $R^5$ and Ar have the same meanings as before. The reaction may be carried out in an aprotic solvent such as dichloromethane in the presence of a base such as triethylamine. Alternatively, in the case that Y represents $NR^3$, amine (3) may be treated sequentially with catechol sulphate and $R^2R^3NH$, in the manner described in WO 02/36555.

Amines (3) may be prepared by condensation of ketones (2) with $tBuSONH_2$ as described above, followed by reduction of the resulting sulfinimide with sodium borohydride (e.g. in methanol solution at 0° C.), then hydrolysis of the resulting sulfinamide (e.g. by treatment with HCl in dioxan and methanol at 0° C.).

The ketones (2) may be prepared by reaction of aldehydes (4) with phosphonium salts (5) in the presence of strong base, followed by hydrolysis of the cyclic ketal group:

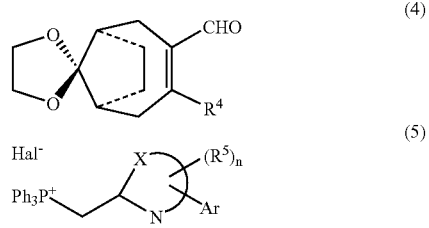

where Hal represents halogen (preferably Cl, Br or I and n, X, Ar, $R^4$ and $R^5$ have the same meanings as before. The reaction may be carried out in an aprotic solvent such as THF at 0° C. in the presence of n-BuLi. Hydrolysis of the cyclic ketal may be effected by treatment with dilute HCl in THF at 60° C.

Aldehydes (4) in which $R^4$ is Cl may be prepared by reaction of ketone (6) with $POCl_3$ and dimethylformamide (DMF):

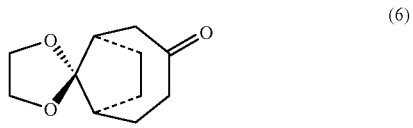

The $POCl_3$ and DMF are typically pre-reacted in dichloromethane solution at 0° C., then refluxed with the ketone in the same solvent.

Aldehydes of formula (4) where $R^4$ is $C_{1-4}$alkyl may be prepared by treatment of the corresponding chlorides (4) ($R^4$=Cl) with the appropriate alkylcopper derivative in THF at −78° C. The alkylcopper reagent may be prepared in situ by pre-reaction of the corresponding alkyllithium with CuI at 0° C.

Ketone (6) may be obtained from bicyclo[4,2,1]non-3-en-9-one (7) by (i) formation of the cyclic ketal, (ii) hydroboration, and (iii) oxidation of the of the resulting cycloalkanols, as described in the Examples included herein.

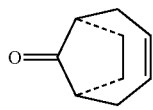
(7)

An alternative strategy for the synthesis of compounds of formula II involves reaction of phosphonium salts (5) with aldehydes (8):

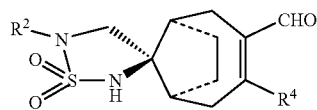
(8)

where $R^2$ and $R^4$ have the same meanings as before. The reaction takes place under the same conditions as the reaction of (5) with (4). Compounds (8) may be obtained from compound (7) via elaboration of its ketone group in the manner described previously for the conversion of ketones (2) to compounds of formula II, followed by hydroboration, oxidation and treatment with $POCl_3$ and DMF as described above for the conversion of (7) to (4).

Phosphonium salts (5) may be obtained by reaction of halides (9)(a) with $Ph_3P$, e.g. in refluxing xylene, while halides (9)(a) are available by conventional routes. In one such route, alcohols (9)(b) are treated with thionyl chloride in dichloromethane at ambient temperature. Alcohols (9)(b) may be prepared by reduction of aldehydes (10), e.g. using sodium borohydride in ethanol:

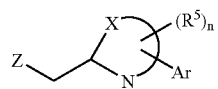
(9)
(a) Z = Hal
(b) Z = OH

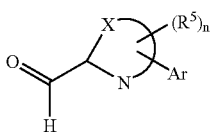
(10)

where n, X, Hal, $R^5$ and Ar have the same meanings as before. Aldehydes (10) may be prepared by conventional techniques of heterocyclic synthesis, as illustrated in the Examples section. An alternative route to the halides 9(a) involves bromination of methyl derivatives (9) (Z=H).

It will be appreciated that where more than one isomer can be obtained from a reaction the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as chiral HPLC, or the formation of diastereomeric pairs by salt formation with an optically active acid, such as di-p-toluoyl-D-tartaric acid and/or di-p-toluoyl-L-tartaric acid, followed by fractional crystallization and regeneration of the free base. The novel compounds may also be resolved by formation of diastereomeric esters or amides, followed by chromatographic separation and removal of the chiral auxiliary. Alternatively, such techniques may be carried out on racemic synthetic precursors of the compounds of interest.

Where they are not commercially available, the starting materials and reagents used in the above-described synthetic schemes may be prepared by conventional means.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1999. The protecting groups may be removed at a convenient subsequent stage using methods known from the art. As an example of this protocol, it is advantageous to alkylate the sulfamide NH group in compounds (8) and its precursors with p-methoxybenzyl chloride and to remove the p-methoxybenzyl protecting group (e.g. by treatment with trifluoroacetic acid) after the remaining synthetic Steps have carried out.

An assay which can be used to determine the level of activity of compounds of the present invention is described in WO01/70677. A preferred assay to determine such activity is described in WO 03/093252.

Alternative assays are described in *Biochemistry,* 2000, 39(30), 8698-8704.

See also, *J. Neuroscience Methods,* 2000, 102, 61-68.

The compounds of the present invention show unexpectedly high affinities as measured by the above assays. Thus the following Examples all had an $ED_{50}$ of less than 100 nM, typically less than 10 nM, and frequently less than 1 nM in at least one of the above assays. In general, the compounds also exhibit good oral bioavailability and/or brain penetration, and are largely free from undesirable biological interactions likely to lead to toxic side effects.

The following examples illustrate the present invention.

EXAMPLES

Intermediate A

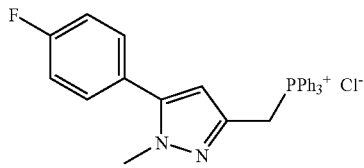

Step 1

5-(4-fluorophenyl)-1-methyl-1H-pyrazol-3-carboxaldehyde dimethyl acetal

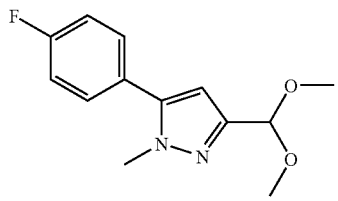

To a solution of lithium diisopropylamide (1.8M in THF, 160 mL, 0.29 mol) at −78° C. was added 4-fluoroacetophenone (17.6 mL, 0.145 mol) in THF (150 mL), dropwise. The reaction was stirred at −78° C. for 1 h before the addition of methyl dimethoxyacetate (17.7 mL, 0.145 mol) in THF (150 mL). The reaction was warmed to 25° C. and stirred for 16 h. The solvent was removed in vacuo and the residue taken up in EtOH (250 mL), acetic acid (17 mL, 0.3 mol) added, followed by methyl hydrazine (8 mL) and the reaction heated to reflux for 2 h. The ethanol was removed in vacuo and the residue extracted with dichloromethane (×3), the organic layer washed with brine, dried over MgSO$_4$ and concentrated. The residue was chromatographed on silica eluting with 50% ethyl acetate/hexanes to give the title compound (more polar isomer) along with its isomer (less polar). 9 g $^1$H NMR (360, CDCl$_3$) δ 7.38 (m, 2H), 7.14 (m, 2H), 6.34 (s, 1H), 5.48 (s, 1H), 3.85 (s, 3H), 3.43 (s, 6H).

Step 2

5-(4-fluorophenyl)-1-methyl-1H-pyrazol-3-carboxaldehyde

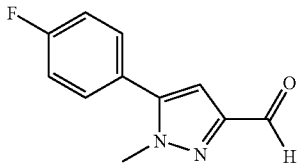

The compound from Step 1 (9 g) was treated with trifluoroacetic acid (30 mL) and water (30 mL). The trifluoroacetic acid was removed in vacuo and the reaction mixture partitioned between ethyl acetate and saturated sodium bicarbonate. The organic layer was washed with saturated sodium bicarbonate (×2), brine and dried over MgSO$_4$. The solvent was removed in vacuo to give a yellow oil which was crystallised from ethyl acetate/hexanes to give the title compound. 4.6 g $^1$H NMR (360, CDCl$_3$) δ 9.97 (s, 1H), 7.38 (m, 2H), 7.20 (m, 2H), 6.80 (s, 1H), 3.95 (s, 3H).

Step 3

[5-(4-fluorophenyl)-1-methyl-1H-pyrazol-3]-methyltriphenylphosphonium chloride

The aldehyde from Step 2 (2.3 g, 11 mmol) was dissolved in ethanol and sodium borohydride (0.832 g, 22 mmol) added, and the reaction stirred at 25° C. for 1 h. The reaction was quenched with ammnonium chloride solution, the ethanol removed in vacuo and the aqueous extracted into ethyl acetate (2×), washed with brine and concentrated to give a yellow oil. The crude alcohol was dissolved in dichloromethane (20 mL), thionyl chloride ( 1.6 mL, 22 mmol) was added and the reaction stirred at 25° C. for 1 h. Water was added and the product extracted into dichloromethane (2×), dried over MgSO$_4$, concentrated and azeotroped with toluene to give a solid. The solid was dissolved in xylene (50 mL) and triphenylphosphine (2.62 g, 10 mmol) added and the reaction heated to reflux for 16 h. The solid formed was filtered off and washed with xylene. The filtrate was heated to reflux for a further 16 h and the solid formed was filtered and washed with xylene. The combined solid gave 2.15 g of the title compound. $^1$H NMR (360, CDCl$_3$) δ 7.84 (m, 6H), 7.7 (m, 3H), 7.64 (m, 6H), 7.22 (m, 2H), 7.07 (m, 2H), 6.38 (d, J=1.7 Hz, 1H), 5.50 (d, J=13.84, 2H), 3.65 (s, 3H).

Intermediate B

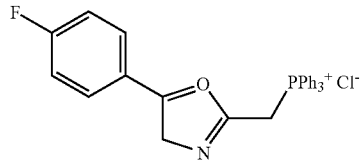

Step 1

5-(4-fluorophenyl)-1,3-oxazole-2-carbaldehyde

A solution of nBuLi (1.6 M in hexane, 3.45 ml, 5.53 mmol) was added dropwise at −78° C. to a stirred solution of 5-(4-fluorophenyl)-1,3-oxazole (0.82 g, 5.03 mmol) in THF (10 ml) (Organic Letters (2001),(3)2, 271-273). The mixture was stirred at −78° C. for 30 minutes and then quenched with DMF (0.43 ml, 5.53 mmol). It was gradually warmed to room temperature, stirred for further 30 minutes, diluted with Et$_2$O (30 ml), then neutralised with 1N HCl. The organic layer was separated, washed with brine (20 ml), dried over MgSO$_4$ and concentrated in vacuo. Purification by chromatography on silica gel eluting with DCM afforded 5-(4-fluorophenyl)-1,3-oxazole-2-carbaldehyde (0.58 g, 60%): δ$_H$ (360 MHz, CDCl$_3$) 7.18 (2H, t, J 8.6 ), 7.58 (1H, s), 7.77-7.81 (2H, m), 9.76 (1H, s); m/z (ES$^+$) 192 (MH$^+$).

Step 2

[5-(4-fluorophenyl)-1,3-oxazole-2-yl]methanol

NaBH$_4$ (138 mg, 3.6 mmol) was added to a solution of 5-(4-fluorophenyl)-1,3-oxazole-2-carbaldehyde (0.58 g, 3.03 mmol) in methanol (10 ml). The mixture was stirred at room temperature for 2 hours, then poured into water (50 ml), extracted with DCM (30 ml), washed with brine (20 ml), dried over MgSO$_4$ and concentrated in vacuo to afford 460 mg (79%) of the title compound: δ$_H$ (360 MHz, CDCl$_3$) 2.57 (1H, m), 4.79 (2H, d, J 5.5) 7.12 (2H, t, J 8.5), 7.24 (1H, s), 7.60-7.64 (2H, m); m/z (ES$^+$) 194 (MH$^+$).

13

Step 3

[5-(4-fluorophenyl)-1,3-oxazole-2-yl]methyltriphenylphosphonium chloride

[5-(4-fluorophenyl)-1,3-oxazol-2-yl]methanol (0.46 g, 2.4 mmol) was dissolved in DCM (5 ml), then Et₃N (0.3 ml, 2.4 mmol) and SOCl₂ (0.35 ml, 4.7 mmol) were added. The reaction mixture was stirred for 1 hour at room temperature under nitrogen. The mixture was diluted with DCM (20 ml) and a saturated solution of Na₂CO₃ (20 ml) was added carefully. The organic layer was separated, washed with brine (20 ml), dried over MgSO₄ and concentrated in vacuo to give a yellow oil. This oil (0.5 g, 2.38 mmol) was treated with an equimolar amount of triphenylphosphine as described for Intermediate A (Step 3) to give the title compound. $\delta_H$ (360 MHz, DMSO) 5.76 (2H, d, J 16.0), 7.29 (2H, t, J 7.0), 7.39-7.46 (2H, m), 7.61 (1H, s), 7.74-7.95 (15H, m).

Intermediate C

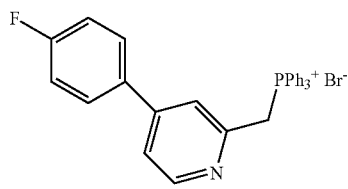

Step 1

4-(4-fluorophenyl)-2-methylpyridine

A mixture of 4-chloro-2-methylpyridine (10 g, 79 mmol) and (4-fluorophenyl)boronic acid (13.2 g, 94 mmol) in DME (150 ml) and 2M Na₂CO₃ (94 ml) was degassed for 5 minutes with a stream of nitrogen before adding Pd(PPh₃)₄ (1.8 g, 2 mol %) and then refluxing overnight. The reaction mixture was cooled to room temperature, diluted with ethyl acetate (30 ml), washed with 4 N NaOH (40 ml) and then with brine (50 ml). The organic layer was then dried over MgSO₄, concentrated in vacuo and purified by chromatography on silica gel eluting with a gradient 30-50% ethyl acetate/hexane to afford 9.0 g of the title compound (61%): $\delta_H$ (360 Mz, CDCl₃) 2.62 (3H, s), 7.16 (2H, t, J 8.5), 7.27 (1H, d, J 5.0), 7.33 (1H, s), 7.58-7.62 (2H, m), 8.53 (1H, d, J 5.0); m/z (ES⁺) 188 (MH⁺).

Step 2

[4-(4-fluorophenyl)pyridin-2-yl]methyltriphenylphosphonium bromide 4-(4-fluorophenyl)-2-methylpyridine (0.4 g, 2.1 mmol) was dissolved in benzene (15 ml), then NBS (570 mg, 3.2 mmol) and benzoylperoxide (52 mg, 10 mol %) were added and the mixture refluxed and under irradiation from a 150 w bulb. After 1 hour another 570 mg of NBS was added. After a further hour the solvent was evaporated under reduced pressure and the residue purified by chromatography on silica gel eluting with 30% ethyl acetate/hexane to afford 57 mg of the title compound which was treated with an equimolar amount of triphenylphosphine as described for Intermediate A to give the title compound; m/z (ES⁺) 448 (M⁺).

14

Example 1

[9-endo]2',3',4',5'-Tetrahydro-5'-(2,2,2-trifluoroethyl) spiro(3-chloro-4-{(E)-2-[5-(4-fluorophenyl)-1-methyl-1H-pyrazol-3-yl]ethenyl}bicyclo[4.2.1]non-3-ene]-9,3'-[1,2,5]thiadiazol-1',1'-dioxide

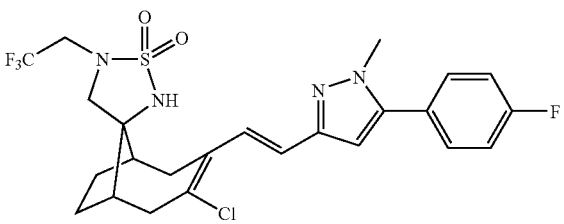

Step 1

[9-endo]2',3',4',5'-Tetrahydro-5'-(2,2,2-trifluoroethyl) spiro(bicyclo[4.2.1]non-3-ene)-9,3'-[1,2,5]thiadiazol-1',1'-dioxide

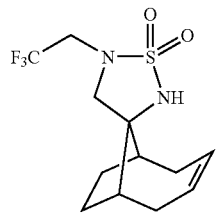

a) Bicyclo[4.2.1]non-3-en-9-one (60 g, 0.44 mol, prepared according to *Synthesis*, 1976, 453), tert-butyl sulphinamide (58.7 g, 0.485 mol), titanium(IV) ethoxide (184.8 mL, 0.88 mol) and anhydrous tetrahydrofuran (900 mL) were heated at reflux under nitrogen for 4hr. The reaction was cooled to room temperature, concentrated in vacuo, poured into brine (1.8 L)/ethyl acetate(54 mL) and stirred vigorously for 1 hr. The mixture was filtered through Hi-flo, washed several times with ethyl acetate and the phases separated. The organic layer was dried over magnesium sulfate and concentrated.

b) Trimethylsulfoxonium iodide (151.3 g, 0.69 mol) was dissolved in anhydrous DMSO (660 mL) under nitrogen and sodium hydride (60% dispersion in oil, 27.5 g, 0.687 mol) added in portions. The reaction was stirred until hydrogen evolution ceased, then the oil from (a) was added as a solution in DMSO and the mixture stirred at 25° C. for 2 h. The reaction mixture was poured into water (1.1 L) and ether (1.1 L). The phases were separated and the aqueous layer extracted with ether (2×550 mL). The combined organic layers were washed with brine, dried over magnesium sulfate and evaporated in vacuo.

c) The oil from (b) (128.4 g, 0.507 mol) was dissolved in anhydrous dichloromethane (770 mL) and trifluoroethylamine (251 g, 2.5 mol) added along with zinc iodide (161.7 g, 0.507 mol). The reaction was heated to reflux and stirred for 16 h., then cooled, diluted with sodium bicarbonate and the product extracted into dicloromethane. The organic layer was dried over magnesium sulfate and concentrated. The residue was chromatographed on silica eluting with 7% MeOH/NH$_3$ (2N)/CH$_2$Cl$_2$ to obtain the pure product.

d) The oil from (c) (28.5 g, 0.115 mol) was dissolved in pyridine (171 mL) and sulfamide (12.1 g, 0.126 mol) added. The reaction was heated to reflux for 3.5 h. The solvent was removed in vacuo and the residue partitioned between HCl (2.5M, 280 mL) and ethyl acetate (280 mL). The aqueous layer was extracted with ethyl acetate (2×280 mL) and the combined organics washed with HCl (2.5M, 280 mL), brine and dried over magnesium sulfate. The solvent was removed in vacuo and the residue was recrystallised from ethyl acetate/isohexanes to yield a cream solid. 19.6 g, $^1$H NMR (500 MHz, DMSO) δ 4.52 (m, 2H), 3.99 (m, 2H), 2.5 (s, 2H), 2.36 (d, J=18 Hz, 2H), 2.27 (brs, 2H), 1.89 (d, J=26 Hz, 2H), 1.35 (m, 2H).

Step 2

[9-endo]2',3',4',5'-Tetrahydro-2'-(4-methoxybenzyl)-5'-(2,2,2-trifluoroethyl)spiro(bicyclo[4.2.1]non-3-ene)9,3'-[1,2,5]thiadiazol-1',1'-dioxide

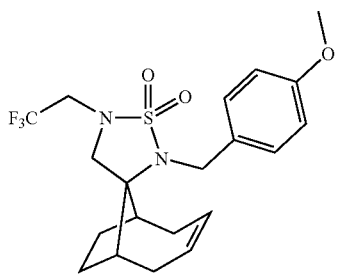

The product of Step 1 (6.6 g, 0.021 mol) was dissolved in acetone (100 mL) and potassium carbonate (4.3 g, 0.031 mol) was added, followed by tetra-n-butylammonium iodide (0.760 g, 2.05 mmol) and p-methoxybenzyl chloride (6.4 g, 0.041 mol). The reaction was stirred at 25° C. under nitrogen for 36 h., filtered and the filtrate was concentrated in vacuo. The residue was recrystallised from ethyl acetate/hexane to obtain a white solid (tetra-n-butylammonium iodide). The mother liquor was concentrated and the residue was treated with ethyl acetate/hexane to obtain the title product as a solid. 5.65 g $^1$H NMR (500 MHz, CDCl$_3$) δ 7.25 (d, 2H), 6.85 (d, 2H), 5.59 (d, 2H), 4.58 (2H, 2H), 3.78 (s, 3H), 3.71 (m, 2H), 3.39 (s, 2H), 2.47 (m, 4H), 2.16 (m, 2H), 1.88 (m, 2H), 1.50 (m, 2H).

Step 3

[9-endo]2',3',4',5'-Tetrahydro-2'-(4-methoxybenzyl)-5'-(2,2,2-trifluoroethyl)spiro(3-hydroxybicyclo[4.2.1]non-3-ene)9,3'-[1,2,5]thiadiazol-1',1'-dioxide

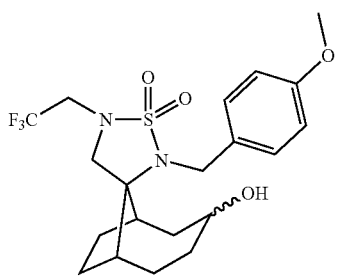

The product of Step 2 (5.65 g, 0.013 mol) was dissolved in anhydrous THF, cooled to 0° C. and borane (1M solution in TBF, 26 mL, 0.026 mol) was added dropwise. The reaction was warmed to 25° C. and then heated to reflux for 2 h. The flask was once again cooled to 0° C. and NaOH (4M, 19.5 mL, 0.078 mol) was added dropwise, followed by hydrogen peroxide (35% w/w, 7.6 mL, 0.078 mol). The reaction was stirred at 25° C. for 16 h. The reaction mixture was partitioned between water and ethyl acetate and the organic layer was washed with water and brine, dried over MgSO$_4$, and the solvent evaporated. The residual oil was chromatographed on silica eluting with 50%-60% ethyl acetate/hexane to provide the title compound (mixture of epimers) as a colourless oil. 4.6 g $^1$H NMR (500 MHz, CDCl$_3$) δ 7.35-7.40 (m), 6.87-6.89 (m), 4.43-4.48 (m), 4.30 (m), 4.09-4.14 (m), 3.79 (s), 3.69-3.81 (m), 3.41-3.43 (m), 3.23-3.32 (m), 2.66 (m), 2.54 (m), 2.04-2.43 (m), 1.33-2.0 (m).

Step 4

[9-endo]2',3',4',5'-Tetrahydro-2'-(4-methoxybenzyl)-5'-(2,2,2-trifluoroethyl)spiro(3-oxobicyclo[4.2.1]non-3-ene)9,3'-[1,2,5]thiadiazol-1',1'-dioxide

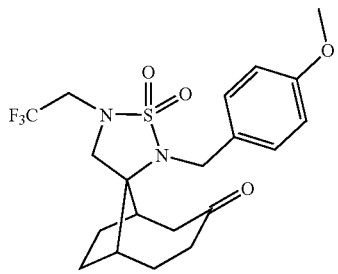

The product of Step 3 (4.6 g, 0.01 mol) was dissolved in dichloromethane (200 mL) and molecular sieves (4 Å, 2.5 g) were added followed by N-methylmorpholine N-oxide (1.8 g, 0.015 mol) and tetrapropylammonium perruthenate (0.151 g, 0.042 mmol). The reaction mixture was stirred under nitrogen for 1.5 h, diluted with ethyl acetate and filtered through a pad of silica with further washings with ethyl acetate. The filtrate was concentrated and the residue chromatographed on silica, eluting with 40%-50% ethyl acetate/hexane to obtain the title compound as an oil which crystallised on standing. 4.0 g $^1$H NMR (500 MHz, CDCl$_3$) δ 7.24 (d, 2H), 6.87 (d, 2H), 4.39 (s, 2H), 3.79 (s, 3H), 3.71-3.74 (m, 2H), 3.38 (dd, 2H), 3.16 (dd, 1H), 2.71 (m, 1H), 2.62 (dt, 1H), 2.50 (m, 2H), 2.35 (dd, 1H), 2.32 (m, 1H), 2.04 (m, 1H), 1.92 (m, 2H), 1.77 (m, 1H), 1.62 (m, 1H).

Step 5

[9-endo]2',3',4',5'-Tetrahydro-2'-(4-methoxybenzyl)-5'-(2,2,2-trifluoroethyl)spiro(3-chloro-4-formylbicyclo[4.2.1]non-3-ene)9,3'-[1,2,5]thiadiazol-1',1'-dioxide

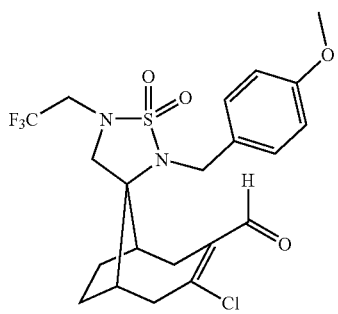

To a dry flask under nitrogen was added dichloromethane (5 mL) and dimethylformamide (0.9 mL, 0.671 mol) and the flask cooled to 0° C. Phosphorus oxychloride (0.9 mL, 0.671 mol) was added dropwise and the reaction warmed to 25° C. and stirred for 15 minutes. The product of Step 4 (1.0 g, 0.224 mol) in dichloromethane (20 mL) was added to the reaction mixture. The flask was heated to 60° C. for 2 h, cooled to 0° C. and water (20 mL) added. The reaction mixture was stirred for 10 minutes and poured into ethyl acetate. The organic layer was collected, washed with saturated sodium bicarbonate solution, brine and dried over $MgSO_4$. The organic layer was evaporated to obtain the title compound along with its regioisomer as an oil. 0.95 g (4:1 ratio of isomers with the desired isomer predominating) $^1H$ NMR (500 MHz, $CDCl_3$) δ 10.17 (s), 9.69 (s), 7.25 (d), 7.06 (d), 6.83-6.88 (m), 4.38-4.55 (m), 3.86 (d), 3.78 (2×s), 3.71 (m), 3.56 (m), 3.33-3.43 (m), 3.15 (m), 2.95 (m), 2.45-2.8 (m), 2.35 (d), 1.9-2.1 (m), 1.8 (m), 1.7 (m), 1.4 (m).

Step 6

[9-endo]2',3',4',5'-Tetrahydro-2'-(4-methoxybenzyl)-5'-(2,2,2-trifluoroethyl)spiro(3-chloro-4-{(E)-2-[5-(4-fluorophenyl)-1-methyl-1H-pyrazol-3-yl]ethenyl}bicyclo[4.2.1]non-3-ene)9,3'-[1,2,5]thiadiazol-1',1'-dioxide

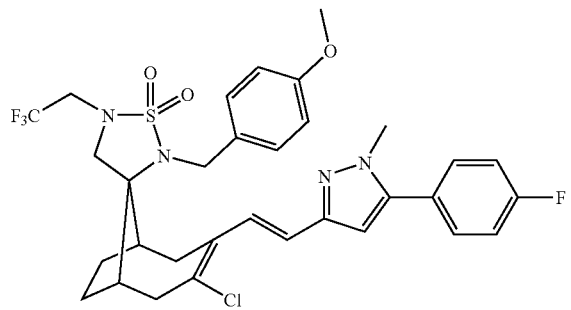

Intermediate A (0.100 g, 0.2 mmol), suspended in THF and cooled to 0° C., was treated with n-butyllithium (2.5M in hexanes, 0.08 mL, 0.188 mol) and the orange solution stirred for 15 minutes at 0° C. The chloro-aldehyde (0.092 g, 0.188 mmol) from Step 5 in THF (1 mL) was added to the ylid and the resulting solution stirred at 0° C. for a further 20 minutes. The reaction mixture was diluted with saturated ammonium chloride solution and ethyl acetate. The organic layer was collected, washed with brine and dried over $MgSO_4$ and concentrated in vacuo. The residue was chromatographed on silica, eluting with 20%-50% ethyl acetate/hexanes to obtain the title product as an oil. 0.040 g $^1H$ NMR (360 MHz, $CDCl_3$) δ 7.38-7.46 (m, 3H), 7.37 (m, 2H), 7.15 (t, 2H), 6.87 (d, 2H), 6.57 (d, 1H), 6.46 (s, 1H), 4.49 (s, 2H), 3.84 (s, 3H), 3.78 (s, 3H), 3.72 (m, 2H), 3.34 (m, 3H), 2.58-2.81 (m, 3H), 1.54-1.89 (m, 3H). MS (m/z) 665 (M+H).

Step 7

The product of Step 6 (0.04 g, 0.006 mmol) was treated with trifluoroacetic acid (3 mL) and the mixture was stirred at 25° C. for 2 h. The reaction mixture was concentrated in vacuo and the residue partitioned between ethyl acetate and saturated sodium bicabonate solution. The organic layer was collected, washed with brine, dried over $MgSO_4$ and evaporated. The residue was chromatographed on silica eluting with 50%-70% ethyl acetate/hexanes to obtain the product as a white solid. 0.012 g $^1H$ NMR (500 MHz, $CDCl_3$) δ 7.45 (d, J=15 Hz, 1H), 7.39 (m, 2H), 7.16 (m, 2H), 6.62 (d, J=15 Hz, 1H), 6.47 (s, 1H), 4.59 (s, 1H), 3.84 (s, 3H), 3.64-3.67 (m, 2H), 3.39 (dd, J=20 Hz, 5 Hz, 2H), 3.15 (d, J=18 Hz, 1H), 2.68-2.79 (ddd, J=10 Hz, 18 Hz, 24 Hz, 2H), 2.56 (m, 1H), 2.48 (m, 1H), 2.37 (m, 1H), 1.87 (m, 2H), 1.72 (m, 1H), 1.6 (m, 1H). MS (m/z) 585 (M+H).

Example 2

[9-endo]2',3', 4',5'-Tetrahydro-5'-(2.2.2-trifluoroethyl)spiro[3-{(E)-2-[5-(4-fluorophenyl)-1-methyl-1H-pyrazol-3-yl]ethenyl}-4-methyl bicyclo[4.2.1]non-3-ene]-9,3'-[1,2,5]thiadiazol-1',1'-dioxide

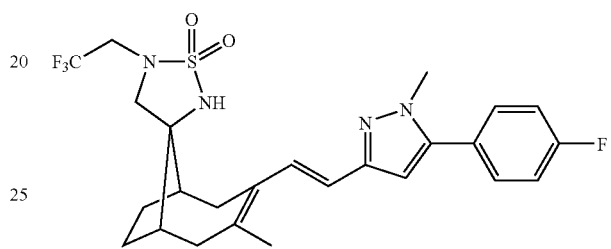

Step 1

[9-endo]2',3',4',5'-Tetrahydro-2'-(4-methoxybenzyl)-5'-(2,2,2-trifluoroethyl)spiro(4-methyl-3-formylbicyclo[4,2,1]non-3-ene)9,3'-[1,2,5]thiadiazol-1',1'-dioxide

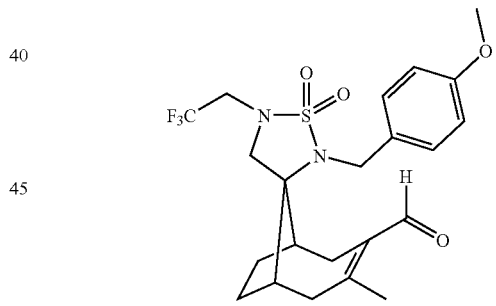

Methyllithium (1.6M in ether, 9 mL, 14 mmol) was added to a suspension of CuI (1.33 g, 7 mmol) in TBF (5 ml) at 0° C. The reaction was stirred at 0° C. for 10 minutes and warmed briefly to 10° C. and then cooled to −78° C. The product of Example 1, Step 5 (2.46 g, 5 mmol) in THF (10 mL) was added and the reaction stirred for 1 h at −78° C. The reaction was quenched with ammonium chloride solution and the product extracted into ethyl acetate. The organic layer was dried over $MgSO_4$ and evaporated. The residue obtained was chromatographed on silica eluting with 20% ethyl acetate/hexanes to obtain the title compound. 0.409 g $^1H$ NMR (500 MHz, $CDCl_3$) δ 10.10 (s, 1H), 7.27 (d, 2H), 6.85 (d, 2H), 4.44(dd, J=25 Hz, 15 Hz, 2H), 3.76 (s, 3H), 3.7 (m, 2H), 3.35 (dd, J=45 Hz, 10 Hz, 2H), 3.24 (d, J=15 Hz, 1H), 3.02 (dd, J=15 Hz, 5 Hz, 1H), 2.75 (t, 1H), 2.52 (t, 1H), 2.23 (m, 4H), 1.85 (m, 1H), 1.69 (m, 1H), 1.46 (m, 1H), 1.32 (m, 1H).

Step 2

The product of Step 1 (0.409 g, 0.9 mmol) was treated as in Example 1 Steps 6 and 7 to provide the title compound (0.055 g). $^1$H NMR (500 MHz, CDCl$_3$) δ 7.39 (m, 2H), 7.25 (d, 2H), 7.15 (m, 2H), 6.47 (d, 1H), 6.38 (s, 1H), 4.52 (s, 1H), 3.82 (s, 3H), 3.63 (m, 2H), 3.38 (m, 2H), 2.65-2.75 (m, 2H), 2.3-2.5 (m, 2H), 1.94 (s, 3H), 1.8 (m, 2H). MS (m/z) 525 (M+H).

Example 3

[9-endo]2',3',4',5'-Tetrahydro-5'-(2,2,2-trifluoroethyl) spiro(3-chloro-4-{(E)-2-[5-(4-fluorophenyl)-1,3-oxazol-2-yl]ethenyl}bicyclo[4.2.1]non-3-ene)-9,3'-[1,2,5]thiadiazol-1',1'-dioxide

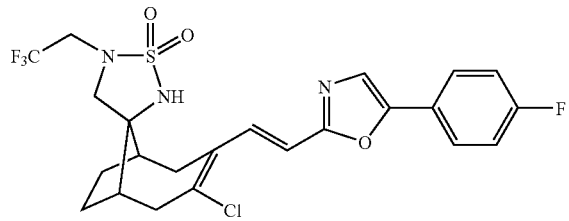

Prepared by the method of Example 1, using Intermediate B in Step 6.

δ$_H$ (400 MHz, CDCl$_3$): 1.73 (1H, m), 1.93 (2H, m), 2.39 (1H, m), 2.53 (1H, m), 2.61 (1H, m), 2.69 (1H, m), 2.73 (1H, m), 2.79 (1H, m), 3.18 (1H, m), 3.42 (2H, q, J 6.0), 3.65-3.69 (2H, m), 4.54 (1H, s), 6,47 (1H, d, J 16.5), 7.13 (2H, t, J 8.5), 7.34 (1H, s), 7.63-7.67 (2H, m), 7.92 (1H, d, J 16.5); m/z (ES$^+$) 532 (MH$^+$).

Example 4

[9-endo]2',3',4',5'-Tetrahydro-5'-(2,2,2-trifluoroethyl) spiro(3-chloro-4-{(E)-2-[4-(4-fluorophenyl)pridin-2-yl]ethenyl}bicyclo[4.2.1]non-3-ene)-9,3'-[1,2,5]thiadiazol-1',1'-dioxide

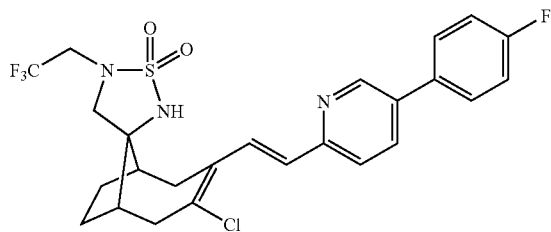

Prepared by the method of Example 1, using Intermediate C in Step 6.

δ$_H$ (500 MHz, CDCl$_3$): 1.75 (1H, m), 1.91 (3H, m), 2.39 (1H, m), 2.52 (1H, m), 2.62-2.68 (1H, m), 2.73-2.87 (2H, m), 3.14-3.20 (1H, m), 3.39-3.45 (2H, m), 3.63-3.69 (2H, m), 4.52 (1H, s), 6.76 (1H, d, J 18.0), 7.19 (2H, t, J 8.5), 7.30-7.32 (1H, m), 7.51 (1H, s), 7.60-7.65 (2H, m), 8.02 (1H, d, J 18.0), 8.61 (1H, d, J 5.5); m/z (ES$^+$) 542 (MH$^+$).

Example 5

N-(-3-Chloro-4-{(E)-2-[5-(4-fluorophenyl)-1-methyl-1H-pyrazol-3-yl]vinyl}bicyclo[4.2.1]non-3-en-9-yl)-N-propylsulfamide

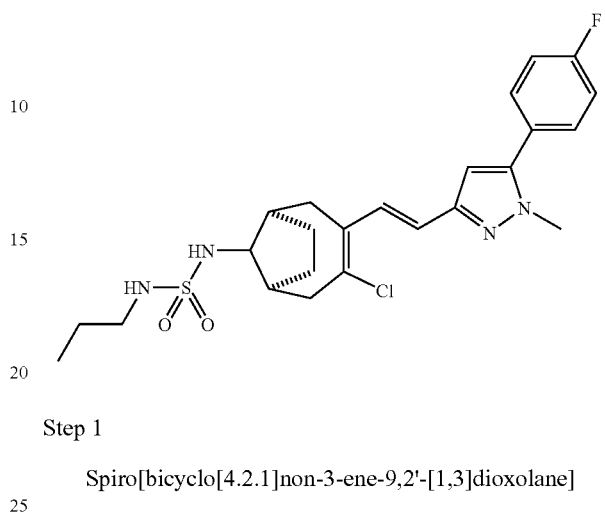

Step 1

Spiro[bicyclo[4.2.1]non-3-ene-9,2'-[1,3]dioxolane]

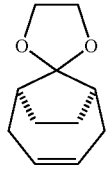

A mixture of bicyclo[4.2.1]non-3-en-9-one (10 g, 73 mmol), ethyleneglycol (12.3 ml, 220 mmol) and p-toluenesulphonic acid monohydrate (100 mg) in toluene (250 ml) was refluxed in a Dean-Stark apparatus for four hours. The reaction mixture was cooled to ambient temperature and sequentially washed with water (3×50 ml) and brine (100 ml). The organic extract was dried over MgSO$_4$ and concentrated in vacuo, to afford spiro[bicyclo[4.2.1]non-3-ene-9,2'-[1,3] dioxolane] (13.12 g, 99.5%).

Step 2

3-{(E)-2-[4-chlorospiro[bicyclo[4.2.1]non-3-ene-9,2'-[1,3]dioxolan]-3-yl]vinyl}-5-(4-fluorophenyl)-1-methyl-1H-pyrazole

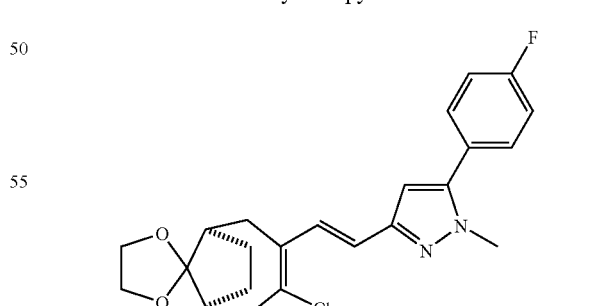

Prepared from the product of Step 1 by procedures analogous to those of Example 1 Steps 3-6. δ$_H$ (400 MHz, CDCl$_3$) 1.31-1.66 (2H, m), 1.81-1.96 (2H, m), 2.04-2.08 (1H, m), 2.15-2.19 (1H, m), 2.53-2.59 (2H, m), 2.65-2.71 (1H, m), 3.12 (1H, d, J 17.0), 3.83 (3H, s), 3.96-3.99 (4H, m), 6.48 (1H, s), 6.62 (1H, d, J 16.5), 7.13-7.18 (2H, m), 7.37-7.42 (2H, m), 7.48 (1H, d, J 16.5).

Step 3

3-Chloro-4-4-{(E)-2-[5-(4-fluorophenyl)-1-methyl-1H-pyrazol-3-yl]vinyl}bicyclo[4.2.1]non-3-en-9-one

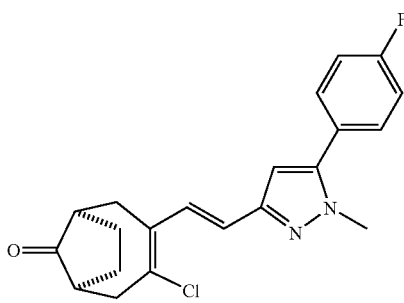

A mixture of 2N hydrochloric acid (100 ml) and the product of Step 2 (18.0 g, 43 mmol) in THF (100 ml) was stirred at 60° C. for 2 hrs. The reaction mixture was basified with saturated sodium hydrogen carbonate and then extracted with ethyl acetate (3×200 ml). The organic extract was washed with brine, dried over MgSO$_4$ and concentrated in vacuo. The residue was purified by flash chromatography eluting with ethylacetate: hexane (1:1) to afford 3-chloro-4-{(E)-2-[5-(4-fluorophenyl)-1-methyl-1H-pyrazol-3-yl]vinyl}bicyclo[4.2.1]non-3-en-9-one (14.96 g, 94%). δ$_H$ (400 MHz, CDCl$_3$) 1.59-1.71 (2H, m), 1.76-1.83 (1H, m), 2.02-2.10 (2H, m), 2.38-2.51 (2H, m), 2.58-2.62 (1H, m), 2.87-2.90 (1H, m), 2.96-3.01 (1H, m), 3.84 (3H, s), 6.49 (1H, s), 6.64 (1H, d, J 16.5), 7.14-7.18 (2H, m), 7.38-7.42 (2H, m), 7.54 (1H, d, J 16.5).

Step 4

N((9Z)-3-chloro-4-{(E)-2-[5-(4-fluorophenyl)-1-methyl-1H-pyrazol-3-yl]vinyl}bicyclo[4.2.1]non-3-en-9-ylidene)-2-methylpropane-2-sulfinamide

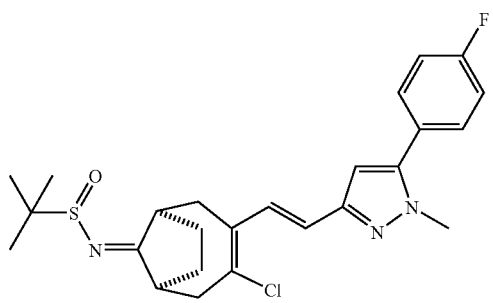

tert-Butylsulphinamide (3.0, 24 mmol) followed by titanium (IV) ethoxide (4.6 ml, 36 mmol) was added to a stirring solution of the product of Step 3 (4.56 g, 11 mmol) in dry THF (10 ml) and the resulting solution was heated to reflux for 18 hrs. The reaction was poured into a stirring solution of brine (200 ml) and then ethyl acetate (100 ml) was added and the mixture filtered through celite. The filtrate was partitioned and the aqueous layer was further extracted with ethyl acetate (2×50 ml). The combined organic extract was washed with brine, dried over MgSO$_4$ and concentrated in vacuo, to afford N((9Z)-3-chloro-4-{(E)-2-[5-(4-fluorophenyl)-1-methyl-1H-pyrazol-3-yl]vinyl}bicyclo[4.2.1]non-3-en-9-ylidene)-2-methylpropane-2-sulfinamide (5.19 g, 99%). m/z (ES$^+$) 474 (MH)$^+$. Compound taken directly onto next Step.

Step 5

N(3-Chloro-4-{(E)2-[5-(4-fluorophenyl)-1-methyl-1H-pyrazol-3-yl]vinyl}bicyclo[4.2.1]non-3-en-9-yl)-2-methyl propane-2-sulfinamide

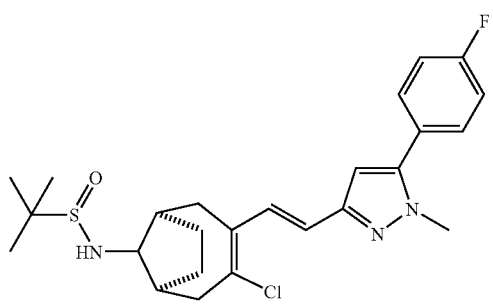

Sodium borohydride (0.83 g, 22 mmol) was added portionwise into a stirring solution of the product of Step 4 (5.19 g, 11 mmol) in methanol (150 ml) at 0° C. The mixture was stirred at 0° C. for 1 hr and then at ambient temperature for a further 2 hrs. The reaction mixture was concentrated in vacuo and diluted with water and extracted with ethyl acetate (3×100 ml). The organic extract was washed with brine, dried over MgSO$_4$ and concentrated in vacuo to afford N(3-chloro-4-{(E)2-[5-(4-fluorophenyl)-1-methyl-1H-pyrazol-3-yl]vinyl}bicyclo[4.2.1]non-3-en-9-yl)-2-methylpropane-2-sulfinamide (5.71 g, 79%). δ$_H$ (400 MHz, CDCl$_3$) 1.20-1.27 (9H, m), 1.86-1.91 (2H, m), 2.40-2.50 (1H, m), 2.56-2.67 (4H, m), 3.06-3.18 (1H, m), 3.30-3.39 (1H, m), 3.67-3.77 (2H, m), 3.82 (3H, s), 6.47 (1H, d, J 5.5), 6.63 (1H, d, J 16.0), 7.15 (2H, t, J, 8.5), 7.38-7.42 (2H, m), 7.47 (1H, d, J 16.0).

Step 6

(3-Chloro-4-{(E)-2-[5-(4-fluorophenyl)-1-methyl-1H-pyrazol-3-yl]vinyl}bicyclo[4.2.1]non-3-en-9-yl)amine

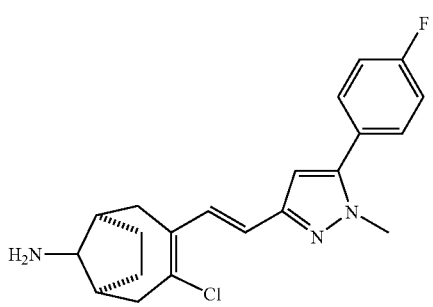

Hydrochloric acid (in dioxane, 4M, 50 ml) was added into a solution of the product of Step 5 (5.71 g, 12 mmol) in methanol (100 ml) at 0° C. The solution was stirred at 0° C. for 1 hr and then at ambient temperature for a further 1 hr. The reaction mixture was concentrated in vacuo, diluted with saturated sodium hydrogen carbonate and extracted with ethyl acetate (3×100 ml). The organic extract were washed with brine, dried over MgSO₄ and concentrated in vacuo, then eluted through an SCX cartridge (50 g) with methanol (100 ml) and then with ammonia in methanol (2M, 50 ml). The fraction containing the product was concentrated in vacuo, to afford (3-chloro-4-{(E)-2-[5-(4-fluorophenyl)-1-methyl-1H-pyrazol-3-yl]vinyl}bicyclo[4.2.1]non-3-en-9-yl)amine (3.76 g, 84%). $\delta_H$ (400 MHz, CDCl₃) 1.33-1.61 (4H, m), 1.74-1.92 (2H, m), 2.15-2.23 (1H, br), 2.30-2.39 (1H, br), 2.54-2.69 (3H, m), 3.12 (1H, d, J 18.0), 3.34 (1H, t, J 6.5), 3.82 (3H, s), 6.47 (1H, s), 6.65 (1H, d, J 16.5), 7.15 (2H, t, J 8.5), 7.37-7.41 (2H, m), 7.47 (1H, d, J 16.5)

Step 7

A mixture of the product from Step 6 (100 mg, 0.27 mmol), triethylamine (110 mg, 1.1 mmol) and propylsulfamoyl chloride (170 mg, 1.1 mmol) in DCM (5 ml) was stirred at ambient temperature for 18 hrs. The reaction mixture was diluted with water (20 ml) and extracted with ethyl acetate (3×20 ml). The organic extracts were washed with brine (50 ml), dried over MgSO₄ and concentrated in vacuo. The residue was purified by flash chromatography eluting with ethyl acetate: hexane (1:4) to afford N-(3-chloro-4-{(E)-2-[5-(4-fluorophenyl)-1-methyl-1H-pyrazol-3-yl]vinyl}bicyclo[4.2.1]non-3-en-9-yl)-N-propylsulfamide (98 mg, 74%). $\delta_H$ (400 MHz, CDCl₃) 0.98 (3H, t, J 7.5), 1.42-1.48 (1H, m), 1.54-1.62 (4H, m), 1.82-1.90 (2H, m), 2.38-2.62 (3H, m), 2.68-2.76 (2H, m), 2.98-3.08 (3H, m), 3.72-3.77 (1H, m), 3.82 (2H, s), 4.13-4.18 (1H, m), 4.33 (1H, d, J 9.0), 6.48 (1H, s), 6.64 (1H, d, J 16.5), 7.12-7.18 (2H, m), 7.37-7.43 (2H, m), 7.45 (1H, d, J 16.5).

The following examples were prepared by the method of Example 5, using the appropriate sulfamoyl chloride or sulfonyl chloride in the final Step:

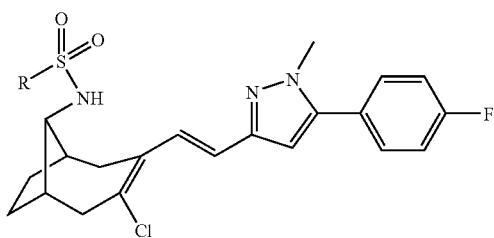

| Example | R |
|---|---|
| 6 | cyclobutylamino |
| 7 | methyl |
| 8 | n-butylamino |
| 9 | pyrrolidin-1-yl |
| 10 | 6-chloropyridin-3-yl |
| 11 | 2,2,2-trifluoroethylamino |
| 12 | (2-methylpropen-3-yl)amino |
| 13 | 4-fluorophenyl |
| 14 | dimethylamino |
| 15 | 2-thienyl |

The invention claimed is:

1. A compound of formula I:

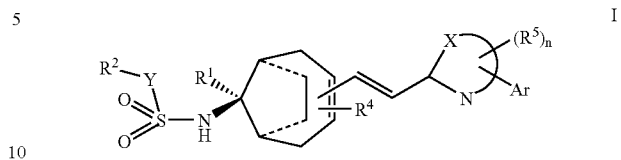

wherein n is 0 or 1;

X completes a 5- or 6-membered heteroaromatic ring bearing the group Ar as a substituent, and also the group $R^5$ as a substituent when n is 1;

$R^5$ represents a hydrocarbon group of 1-5 carbon atoms which is optionally substituted with up to 3 halogen atoms;

Ar represents phenyl or 6-membered heteroaryl, either of which bears 0-3 substituents independently selected from halogen, $CF_3$, $CHF_2$, $CH_2F$, $NO_2$, $CN$, $OCF_3$, $C_{1-6}$alkyl and $C_{1-6}$alkoxy;

Y represents a bond or $NR^3$;

$R^1$ represents H, or when Y represents $NR^3$, $R^1$ and $R^3$ may together represent —$CH_2$—;

$R^2$ represents a hydrocarbon group of 1-10 carbon atoms which is optionally substituted with up to 3 halogen atoms, or heteroaryl of 5 or 6 ring atoms optionally bearing up to 3 substituents independently selected from halogen, $CF_3$, $CHF_2$, $CH_2F$, $NO_2$, $CN$, $OCF_3$, $C_{1-6}$alkyl and $C_{1-6}$alkoxy; or when Y represents $NR^3$, $R^2$ and $R^3$ together may complete a heterocyclic ring of up to 6 members which optionally bears up to 3 substituents independently selected from halogen, $CF_3$, $CHF_2$, $CH_2F$, $NO_2$, $CN$, $OCF_3$, $C_{1-6}$alkyl and $C_{1-6}$alkoxy;

$R^3$ represents H or $C_{1-4}$alkyl, or together with $R^1$ represents —$CH_2$—, or together with $R^2$ completes a heterocyclic ring as defined above; and $R^4$ represents halogen or $C_{1-4}$alkyl;

or a pharmaceutically acceptable salt thereof.

2. A compound according to claim 1 of formula II:

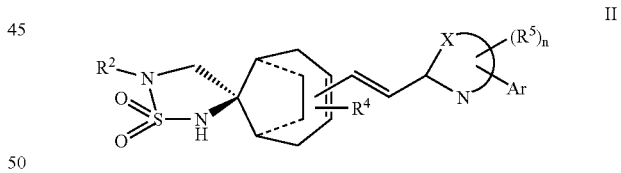

or a pharmaceutically acceptable salt thereof;

where n, X, $R^2$, $R^4$, $R^5$ and Ar are as defined in claim 1.

3. A compound according to claim 1 wherein Y is a bond and $R^2$ is hydrocarbon of up to 6 carbon atoms, optionally bearing up to 3 fluorine or chlorine substituents, or 5-or 6-membered heteroaryl which is optionally substituted as defined in claim 1.

4. A compound according to claim 1 wherein Y represents $NR^3$ and either $R^3$ is H and $R^2$ represents alkyl, alkenyl, cycloalkyl or cycloalkylalkyl of up to 6 carbon atoms which is optionally substituted with up to 3 fluorine atoms; or $R^2$ and $R^3$ complete a heterocyclic ring.

5. A compound according to claim 2 wherein $R^2$ represents alkyl, alkenyl, cycloalkyl or cycloalkylalkyl of up to 6 carbon atoms which is optionally substituted with up to 3 fluorine atoms.

6. A compound according to claim 1 wherein X completes a heteroaryl group selected from include 5-aryl-1-methylpyrazol-3-yl, 5-aryloxazol-2-yl, 4-arylpyridin-2-yl, 1-arylimidazol-4-yl, and 1-aryl-[1,2,4]triazol-3-yl, where "aryl" refers to the group Ar as defined in claim 1.

7. A pharmaceutical composition comprising a compound according to claim 1 and a pharmaceutically acceptable carrier.

* * * * *

UNITED STATES PATENT AND TRADEMARK OFFICE
CERTIFICATE OF CORRECTION

PATENT NO. : 7,452,899 B2
APPLICATION NO. : 10/566486
DATED : November 18, 2008
INVENTOR(S) : Michela Bettati et al.

It is certified that error appears in the above-identified patent and that said Letters Patent is hereby corrected as shown below:

At column 5, line 18, "thiathiazolyl" should read "thiazolyl".

Signed and Sealed this

Sixth Day of July, 2010

David J. Kappos
*Director of the United States Patent and Trademark Office*